United States Patent [19]

Beaucamp et al.

[11] 4,080,262

[45] Mar. 21, 1978

[54] STABILIZING AGENT FOR ENZYMES

[75] Inventors: Klaus Beaucamp, Tutzing; Helmut Lill, Wielenbach, both of Germany

[73] Assignee: Boehringer Mannheim GmbH, Mannheim-Waldof, Germany

[21] Appl. No.: 762,893

[22] Filed: Jan. 26, 1977

Related U.S. Application Data

[63] Continuation-in-part of Ser. No. 645,113, Dec. 29, 1975, abandoned.

[30] Foreign Application Priority Data

Jul. 11, 1974 Germany ............................. 2433454

[51] Int. Cl.² ............................................... C07G 7/00
[52] U.S. Cl. ........................................ 195/63; 195/68; 260/112 R

[58] Field of Search ............................. 195/63.65, 68; 260/112 R; 426/656

[56] References Cited

U.S. PATENT DOCUMENTS

| | | | |
|---|---|---|---|
| 3,051,627 | 8/1962 | Bradford et al. | 195/63 |
| 3,185,675 | 5/1965 | Schmitz et al. | 260/112 R |
| 3,914,450 | 10/1975 | Robbins et al. | 260/112 R X |

Primary Examiner—Lionel M. Shapiro
Attorney, Agent, or Firm—Burgess, Dinklage & Sprung

[57] ABSTRACT

Enzymes, particularly labile enzymes, and most particularly microorganism derived labile enzymes, are stabilized by adding thereto a stabilizing agent comprising a protein fraction obtained by extracting yeast with water at 80° to 100° C., mixing the clear extract with 5 – 20% wt./vol. trichloracetic acid and separating the precipitate obtained.

9 Claims, No Drawings

STABILIZING AGENT FOR ENZYMES

This is a continuation in part of application Ser. No. 645,113 filed Dec. 29, 1975 now abandoned.

This invention relates to a stabilizing agent for enzymes, particularly for labile enzymes.

Enzymes are of increasing importance in analytical processes, as well as in preparative chemistry. However, their main advantage of being extraordinary specifically effective as biocatalysts is countered by the disadvantage of great sensitivity. Because of this instability, many enzymes cannot be used at all for technical or analytical purposes and other enzymes can, because of their instability, only be obtained in such poor yields that the high costs of obtaining them severely restricts their technical use.

Admittedly, numerous stabilizing agents have already been found but many of them are only effective for particular enzymes. For example, it is known that SH group-containing enzymes, the inactivation of which is due to an oxidation of the SH group, are stabilized by the addition of SH groupcontaining stabilizers. Another known stabilizing agent for enzymes is polyvinyl-pyrrolidone. However, for a whole series of enzymes, hitherto no sufficiently effective stabilizing agents have been found.

The present invention provides a stabilizing agent which is especially suitable for labile enzymes and particularly for those which frequently occur in micro-organisms.

The stabilizing agent of the present invention comprises a protein fraction obtainable by the extraction of yeast with water at a temperature of about 80° to 100° C., mixing the clear extract with 5 - 20% wt./vol. trichloroacetic acid and separation of the precipitate obtained.

The stabilizing agent according to the present invention, which, as mentioned above, can be obtained from yeast and especially from bakers' yeast, has a proteinaceous nature and is especially stable towards the action of heat and acids. Thus, for example, the stabilizing protein fraction according to the present invention can be boiled for 30 to 60 minutes, precipitated with strong protein-precipitating acids and treated with organic solvents without its stabilizing properties thereby being lost.

The stabilizing agent according to the present invention is capable of stabilizing not only purified, crystallized enzymes but also crude enzymes. Consequently, it can be added not only to a purified enzyme preparation for the improvement of its storage stability but can also be added during the working up of enzyme-containing raw materials in order to prevent or reduce losses of the desired enzymes during the purification thereof.

The agent according to the present invention can be used in solid form or also in the form of a solution in a solvent which is compatible with the enzyme to be stabilized and preferably in the same solvent in which the enzyme to be stabilized is or is to be dissolved or suspended.

The amount of stabilizing agent added, calculated as the weight of the stabilizing protein added, is preferably between about 0.1 to 1000 fold the weight of the enzyme to be stabilized. In the case of labile enzymes which are present in very low concentrations in a biological starting material, additions considerably greater than the above-mentioned upper limit can also be expedient in order to ensure a sufficiently high stabilizer concentration in the solution mixture which contains the labile enzyme.

The stabilizing agent according to the present invention can be used directly in the form in which it is precipitated with trichloroacetic acid. However, in many cases, it is preferable again to dissolve the trichloroacetic solid precipitate at about neutral pH and to subject it to further purification for the removal of unnecessary ballast material. The further purification preferably comprises an ethanol fractionation, the precipitate obtained with an ethanol addition of from 45 to 90% being recovered. This precipitate can, in turn, be subjected to still further purification by dissolving it in a buffer solution at about neutral pH, followed by dialysis and subsequent chromatography over a chromatographic agent conventionally employed in the high purification of proteins, for example diethylaminoethyl-cellulose or a cross-liked dextran, such as Sephadex and DEAE Sephadex. The best stabilizing action is achieved at pH values above 5. Therefore, the stabilizing agent according to the present invention is preferably employed at a neutral to weakly alkaline pH value.

As already mentioned, the stabilizing agent according to the present invention can be used for the stabilization of labile enzymes of any origin. However, it is preferably used for enzymes originating from micro-organisms since the best stabilizing action has been observed.

Especially labile enzymes which can be stabilized with the stabilizing agent according to the present invention include, for example, glycerokinase (GK), glucose-6-phosphatedehydrogenase (G-6-PDH), aldehyde dehydrogenase and glucose oxidase from microorganizms and malate dehydrogenase from aminal tissues.

A special advantage of the stabilizing agent according to the present invention is that it can also be obtained from waste material. Yeast which has been worked up for the recovery of co-enzymes or of other component materials has hitherto only been of use in agriculture. Since the stabilizing agent according to the present invention can be obtained in an extremely simple manner from this material, an especially readily available source of raw material is provided by this waste yeast material.

Because of its chemical inertness, the new stabilizing agent does not, as a general rule, disturb the biocatalytic activity of enzymes stabilized therewith. The stabilizing agent can be used in solid form or as a solution in an appropriate solvent, preferably in a buffer with a pH value above 5. In the form of a solution, its protein concentration is preferably from about 5 to about 200 mg./ml.

The following examples are given for the purpose of illustrating the present invention.

EXAMPLE 1

A. Recovery of the stabilizing agent.

Hot yeast slurry from waste yeast which was obtained in the extraction of soluble low molecular weight cell content materials (co-enzymes and nucleotides) was mixed with an equal volume of hot water and left to stand for 30 minutes at 80° - 90° C. The batch was subsequently centrifuged and the supernatant, after concentration, mixed with 15% by weight of trichloroacetic acid. The batch was subsequently stirred for 20 hours at ambient temperature.

B. Additional purification, if desired.

The resultant suspension was centrifuged and the precipitate recovered. According to the present invention, it can be used directly as a stabilizing agent. The pricipitate obtained as above was taken up in 0.1M phosphate buffer (pH 7.0) and subsequently adjusted to a pH of 7.0 with an aqueous solution of potassium hydroxide. A clear solution was thereby obtained which was then subjected to an ethanol fractionation between 45 and 90% ethanol, at a temperature of +4° C.

The precipitate obtained by the ethanol precipitation was, after centrifuging, taken up in 0.01M phosphate buffer (pH 7.0) and dialyzed overnight against the same buffer.

For further optional purification, the dialyzed solution was applied to a diethylaminoethyl-Sephadex column. It was washed with 0.02M phosphate buffer (pH 7.0). The eluate contained subfractions (A and B) of the stabilizing agent in concentration of from 30 – 40 mg/ml. and was used for the experiments described in the following examples.

EXAMPLE 2

10 mg. glycerokinase (Boehringer Mannhein GMBH, Mannheim, Germany, Catalog No. 15746) were dissolved in 4 ml. 0.05M phosphate buffer (pH 7.0) and incubated for 18 hours at 30° C. in the presence of the stabilizing agent purified as above. The original activity was taken as being 100%. The residual activity in two experiments can be seen from the following Table 1:

TABLE 1

| Experiment | 1 | 2 |
|---|---|---|
| stabilizing agent | — | 0.2 ml. |
| residual activity of the GK | 20% | 65% |

The above results show that, with the use of the stabilizing agent according to the present invention, a 3.5 fold activity was obtained.

A similar result was obtained when this experiment was repeated using G-6-PDH (Boehringer Manheim catalog No. 15303).

EXAMPLE 3

In order to demonstrate that the addition of the stabilizing agent according to the present invention also brings about a stablization during enzyme purification in the case of a known, critical step, in an initial stage in the isolation of glycerokinase (GK) from *Candida mycoderma* (the purity amounted to about one third of that of the final stage), the stabilizing agent according to the present invention was added.

Here again, the original activity prior to incubation was taken as being 100%. The remaining residual activity after 17 hours incubation at 25° C- can be seen from the results given in the following Table 2.

TABLE 2

| Experiment | 1 | 2 |
|---|---|---|
| stabilizing agent | — | 0.4 ml. |
| residual activity of the crude GK | 1.5% | 100% |

EXAMPLE 4

2 g. Aspergillus niger dry powder were suspended in 20 ml. 0.1M phosphate buffer (pH 7.0) and treated with ultrasonic waves for 5 minutes. Subsequently, the batch was centrifuged for 10 minutes. 2.5 ml. of the supernatant were mixed with 0.5 ml. of pure glycerokinase suspension (Boehringer Mannheim catalog No. 15746) and the solution divided up into 0.5 ml. portions. After the addition of the stabilizing agent, some of the samples were incubated for 44 hours at 25° C. As in the case of the above-described experiments, the activity of the enzyme prior to incubation was taken as being 100%. The residual activities were measured. The results obtained are shown in the following Table 3.

TABLE 3

| Experiment | 1 | 2 | 3 |
|---|---|---|---|
| stabilizing agent | — | 0.05 ml. | 0.1 ml. |
| residual activity of the GK | 32% | 83% | 97% |

The above results show that this sensitive enzyme from *Candida mycoderma* is rapidly inactivated in the crude extract from various micro-organisms and that this inactivation is almost completely prevented by the stabilizing agent according to the present invention obtained from yeast.

EXAMPLE 5

Enzymes from the tissues of animal organs also display instabilities in solution which can be attributed to the action of contaminating proteases. This can be demonstrated by using malate dehydrogenase (MDH) from cardiac muscle as an example.

2 ml. amounts of malate dehydrogenase (8 mg./ml.) in 0.2M potassium phosphate buffer (pH 7.6) were incubated for 4 days at 33° C. 0.1% sodium azide was added in order to prevent bacterial growth.

The activity of the enzyme prior to incubation was taken as being 100%. The residual activities were taken as percentages of the initial value. The results obtained are given in the following Table 4.

TABLE 4

| Experiment | 1 | 2 |
|---|---|---|
| stabilizing agent | — | 4 m.g. |
| residual activity of the MDH | 37% | 64% |

The above results show that the stabilizing agent is also able to inhibit proteases from animal tissues and can thus stabilize certain labile enzymes. A certain part of the MDH activity is apparently lost irreversibly due to denaturing brought about by prolonged temperature stressing.

EXAMPLE 6

The isolation of enzymes from *Bacillus subtilis* are especially endangered by the proteases which are abundant in this micro-organism. This also applies to enzymes from *Bacillus subtilis* spores, as is demonstrated using, as an example, glucose dehydrogenase (gluc-DH):

10 g. *B. substilis* spores (wet weight) were mixed with 30 ml. 0.01M phosphate buffer (pH 6.0). 9 ml. of this suspension were grinded in a mixer with 16 ml. glass beads. The crude extract obtained was incubated overnight at 25° C. The activity of the enzymes prior to the incubation was taken as being 100%. The residual activities were determined and are given in the following Table 5 as percentages of the initial value:

TABLE 5

| Experiment | 1 | 2 | 3 | 4 |
|---|---|---|---|---|
| Stabilizing Agent, subfraction A | — | 0.5 ml. (26 mg/ml) | — | — |
| Stabilizing Agent, subfraction B | — | — | 0.5 ml. (4.4 mg/ml) | — |
| Stabilizing Agent, subfraction A&B | — | — | — | 0.5 ml. A (26 mg/ml) 0.5 ml. B (4.4 mg/ml) |
| residual activity of the glue-DH 2nd crude extract | 0% | 40% | 5% | 80% |

The above results show that the stabilizing agent, subfractions A and B are able to stabilize the most effectively in admixture the glucose dehydrogenace from *B. subtilis* spores, even in a crude extract.

EXAMPLE 7

This example demonstrates the stabilization of a solution of aldehyde dehydrogenase from bakers' yeast.

2.7 ml. amounts of enzyme (80 U) were mixed with 2.7 mg. glutathione, Volume : 1 ml. Incubation period: 1 month at 33° C. The results obtained are shown in the following Table 6.

TABLE 6

| Expt. No. | Stabilizer | Residual activity |
|---|---|---|
| 1 | 0.1% sodium azide; pH 6.0 | 0% |
| 2 | 50% glycerol; pH 6.0 0.1% sodium azide | 4.7% |
| 3 | 50% glycerol; pH 7.0 | 0.9% |
| 4 | 50% glycerol; pH 6.2 0.27% mg. stabilizing agent, subfraction A&B | 26.0% |
| 5 | 50% glycerol; pH 6.2 2.7 mg. stabilizing agent, subfraction A&B | 28.0% |

EXAMPLE 8

This example demonstrates the stabilization of a salt-free solution of glyceraokinase from *Candida mycoderma*.

80 ml. Pure glycerokinase (5 mg./ml.) were desalted over a molecular sieve based on dextran (volume 200 ml.). Subsequently, the protein concentration was adjusted with water to 5 mg./ml. The results obtained after incubation at 33° C. in the presence of various stabilizers are shown in the following Table 7.

TABLE 7

| Expt. No. | Incubation batch | Residual Activity incubation 1 day, 33° C | Residual Activity incubation 2 days, 33° C |
|---|---|---|---|
| 1 | 1 ml. glycerokinase (5 mg.) | 27% | 0% |
| 2 | 1 ml. glycerokinase (5 mg.) + 5 mg. stabilizing agent, subfraction A | 73% | 36% |
| 3 | 1 ml. glycerokinase (5 mg.) + 0.9 mg stabilizing agent, subfraction B | 50% | 0% |
| 4 | 1 ml. glycerokinase (5 mg.) + 5 mg. stabilizing agent, subfraction A + 0.9 mg. stabilizing agent, subfraction B | 73% | 41% |

EXAMPLE 9

This example demonstrates the stabilization of glucose oxidase (GOD) from mold fungus.

Glucose oxidase (1 mg./ml.) in 0.01M potassium phosphate buffer (pH 7.0) was incubated for 16 hours at 25° C. with and without stabilizing agent. The results obtained are shown in the following Table 8.

TABLE 8

| Expt. No. | Incubation batch | Residual activity |
|---|---|---|
| 1 | 1 ml. (1 mg. GOD) | 80 % |
| 2 | 1 ml. (1 mg. GOD; 0.5 mg. stabilizing agent, subfraction A + B) | 100 % |

It will be understood that the specification and examples are illustrative but not limitative of the present invention and that other embodiments within the spirit and scope of the invention will suggest themselves to those skilled in the art.

What is claimed is:

1. Stabilizing agent for labile enzymes comprising a precipitated protein fraction of yeast extracted with water at 80° to 100° C. and mixed with 5 to 20% wt./vol. trichloroacetic acid.

2. Stabilizing agent as claimed in claim 1 in the form of a solution having a pH value of about 5.

3. Stabilizing agent as claimed in claim 2 wherein said solution has a protein content of from 5 to 200 mg/ml.

4. Stabilized enzyme composition comprising a labile enzyme and a stabilizing agent as claimed in claim 1.

5. Stabilized enzyme composition comprising a labile enzyme and a stabilizing agent as claimed in claim 2.

6. Stabilized enzyme composition comprising a labile enzyme and a stabilizing agent as claimed in claim 3.

7. Process for the preparation of a stabilizing agent as claimed in claim 1 which process comprises extracting yeast waste with water at a temperature of 80° to 100° C., mixing the clear extract obtained with 5 to 20% wt./vol. trichloroacetic acid, separating off the precipitate comprising the stabilizing agent.

8. Process claimed in claim 7 further comprising dissolving the said precipitate in water at a substantially neutral pH, subjecting the resultant solution to a fractional ethanol precipitation, recovering the precipitate obtained with from 45 to 90% ethanol, taking up said precipitate in a buffer with a substantially neutral pH and dialyzing said precipitate against said buffer.

9. Process as claimed in claim 8 wherein the dialyzed solution is subjected to chromatographic purification.

* * * * *

UNITED STATES PATENT AND TRADEMARK OFFICE
CERTIFICATE OF CORRECTION

PATENT NO. : 4,080,262
DATED : March 21, 1978
INVENTOR(S) : Klaus Beaucamp et al It is certified that error appears in the above-identified patent and that said Letters Patent are hereby corrected as shown below:

ON THE TITLE PAGE, delete

" [30]  Foreign Application Priority Data

Jul. 11, 1974 Germany ..........2433454".

Signed and Sealed this

Ninth Day of June 1981

[SEAL]

Attest:

RENE D. TEGTMEYER

Attesting Officer     Acting Commissioner of Patents and Trademarks